United States Patent
Verri et al.

(10) Patent No.: US 12,420,222 B2
(45) Date of Patent: *Sep. 23, 2025

(54) FILTER ASSEMBLY AND CONTAINER FOR COLLECTING A BODY FLUID CONTAINING THE SAME

(71) Applicant: Fresenius Hemocare Italia S.R.L., Mirandola (IT)

(72) Inventors: Paolo Verri, Carpi (IT); Matteo Boselli, San Felice sul Panaro (IT); Laura Zambianchi, Reggio Emilia (IT)

(73) Assignee: Fresenius Hemocare Italia S.R.L., Mirandola (IT)

( * ) Notice: Subject to any disclaimer, the term of this patent is extended or adjusted under 35 U.S.C. 154(b) by 481 days.

This patent is subject to a terminal disclaimer.

(21) Appl. No.: 17/902,217

(22) Filed: Sep. 2, 2022

(65) Prior Publication Data
US 2023/0074586 A1    Mar. 9, 2023

(30) Foreign Application Priority Data

Sep. 6, 2021    (EP) .................................... 21195036

(51) Int. Cl.
| | |
|---|---|
| *B01D 39/16* | (2006.01) |
| *A61M 1/00* | (2006.01) |
| *A61M 1/02* | (2006.01) |
| *A61M 1/36* | (2006.01) |

(52) U.S. Cl.
CPC ....... *B01D 39/1623* (2013.01); *A61M 1/0281* (2013.01); *A61M 1/3627* (2013.01); *A61M 1/60* (2021.05); *B01D 2239/0613* (2013.01); *B01D 2239/0618* (2013.01); *B01D 2239/0627* (2013.01); *B01D 2239/0636* (2013.01)

(58) Field of Classification Search
CPC .... A61M 1/3627; A61M 1/3632; A61M 1/60; A61M 1/0281; B01D 19/02; B01D 2239/1216; B01D 2239/0654; B01D 39/1623; B01D 2239/065; B01D 2239/0627; B01D 2239/0618; B01D 2239/0613; B01D 35/30
USPC .......................... 210/496, 485, 406; 604/6.09
See application file for complete search history.

(56) References Cited

U.S. PATENT DOCUMENTS

| | | |
|---|---|---|
| 8,172,818 B2 | 5/2012 | Locke et al. |
| 8,241,264 B2 | 8/2012 | Sjogren et al. |
| 10,004,840 B2 | 6/2018 | Zambianchi et al. |
| (Continued) | | |

FOREIGN PATENT DOCUMENTS

| | | | |
|---|---|---|---|
| EP | 3583962 A1 * | 12/2019 | .......... A61M 1/0052 |
| JP | 2021069733 A | 5/2021 | |

OTHER PUBLICATIONS

Extended European Search Report and Opinion for European Application No. 21195036.5 mailed Feb. 2, 2022.

*Primary Examiner* — Claire A Norris
(74) *Attorney, Agent, or Firm* — Cook Alex Ltd.

(57) ABSTRACT

The present invention relates to a filter assembly for filtering a body fluid comprising a filter holder and a filter system downstream of the filter holder; wherein the filter system and the filter holder are in contact with each other, wherein the filter system comprises a cuboid frame structure with six rectangular surface areas A1-A6, and wherein five of the six surface areas A1-A5 are covered by a filtering media, and wherein the sixth surface area A6 is in contact with the filter holder.

19 Claims, 2 Drawing Sheets

(56) References Cited

U.S. PATENT DOCUMENTS

| | | | |
|---|---|---|---|
| 2016/0354530 A1* | 12/2016 | Peticca | A61M 1/3623 |
| 2021/0187176 A1 | 6/2021 | Zambianchi et al. | |
| 2022/0226550 A1* | 7/2022 | Zambianchi | A61M 1/0281 |

* cited by examiner

FILTER ASSEMBLY AND CONTAINER FOR COLLECTING A BODY FLUID CONTAINING THE SAME

The present application claims the benefit of and priority to European Patent Application Serial No. 21195036.5, filed Sep. 6, 2021, the contents of which are incorporated herein by reference.

The present invention relates to a filter assembly, to an appropriate use of such a filter assembly, and to a container for collecting a body fluid comprising such filter assembly.

Filtering assemblies known from prior art are used to filter different types of fluids, e.g. body fluids, for removing aggregates, particles or specific cells from said fluids. A particular appropriate application of filter assemblies is the filtration of blood. Whole blood or blood components may be separated and further processed for a variety of uses, particularly for use as transfusion products.

Filtering assemblies are also used in auto transfusion processes during surgeries procedures; i.e. blood of a patient is recovered during surgery and re-infused into the patient. This is also known as intraoperative blood salvage, or autologous blood transfusion or cell salvage. It has been used for many years and gained greater attention over time as risks associated with allogenic (separate-donor) blood transfusion have seen greater publicity and become more fully appreciated. Several medical devices have been developed to assist in salvaging the patient's own blood in the perioperative setting. The procedure is frequently used in cardiothoracic and vascular surgery, during which blood usage has traditionally been high.

Whole blood recovered during surgery, but being exposed to surgery, air etc has different characteristics than blood collected in a blood bank from a donor for allogeneic transfusion purpose. For example, blood salvage requires a removal of blood clots, non-cellular substances, such as drugs or fluids used during surgery, bone fragments and surgery debris.

Autologous blood recycling or intraoperative blood salvage is often accompanied by foam formation. Foam formation is related to collection or transportation of blood in presence of air in large tubes (e.g. collected with Yankauer cannulae) and thus related to turbulence in the suction process.

One approach to avoid foam formation in shed blood is the use of antifoam agents in reservoirs where shed blood is collected for autotransfusion or extracorporeal circulation. In the past polydimethylsiloxane (PDMS)—hydrophobed silica was widely used as antifoam. However, PDMS is leached into the blood, where it emulsifies. It is presumed that most of it will be found in the waste after the washing procedure, but it cannot excluded that part of it is found in the Red Cell Concentrate that is autotransfused to the patient. Even though PDMS-hydrophobed silica is non-toxic it was associated as a possible source for emboli due to capillaries blockage and postoperative deaths and is no longer used as antifoam. Thus, nowadays only PDMS without silica is used. The defoaming principle remains the same for PDMS, while the physical way of action, a silica particle that "breaks" the bubble is no longer applied for medical devices, but is still used in non-medical defoaming.

An alternative antifoaming concept is described in WO2020/254871 A1 using a defoaming layer as part of the filter system. Said defoaming layer is made of a monofilament woven open mesh fabric and with an embossed three dimensional structure configured for entrapping foam built up in the body fluid.

The filtering assemblies as for example described above are typically used in specific body fluid collecting containers, in particular blood-collecting containers.

These containers serve for collecting blood during a surgical intervention of a patient. Afterwards, the blood is processed (washed) in order to remove undesired components of the blood and to increase the concentration of red blood cells in the blood. After processing the blood, it can be auto-transfused to the patient to avoid the necessity of providing the patient with blood donations.

The filtering assembly may be formed as a bag or pouch that is manually tied to the top cover of the container.

The filtering assembly may be also designed a filter module that with a skeletal structures. The filter material or filter layers are arranged inside the skeletal structure (WO 2020/254871 A1; WO 2019/243439 A1). A disadvantage of the later arrangement is a reduced surface filter area since only the side walls of said filter module are covered by a filter material. This causes a an increased collection time of filtered blood, what is in particular relevant for low blood volumes.

It is thus an object of the present invention to provide a filter system that allows for an reduced collection time without or reduced foam formation in filtered body fluids, such as shed blood.

This object is achieved by a filter assembly having the features explained in the following.

Accordingly, a filter assembly for filtering a body fluid comprising a filter holder and a filter system downstream of the filter holder, wherein the filter system and the filter holder are in contact with each other or are connected to each other; i.e. the filter holder holds the filter system.

The terms "downstream" and "upstream" refer to a flow direction of a fluid to be filtered by the filter assembly. Thus, the fluid to be filtered contacts at first the defoaming layer followed by the mesh filter layer.

The filter system comprises a cuboid frame structure with six rectangular surface areas A1-A6, wherein five of the six surface areas A1-A5 are covered by a filtering media, and wherein the sixth surface area A6 is in contact with the filter holder. In particular, the frame structure may be overmoulded with filter layers.

Such a filter assembly can well be used for filtering blood and other body fluids. In this case, the body fluid flows through an opening in the filter holder into the interior of the filter system and through the filtering media into a blood collecting canister. Since five of the sixth rectangular areas of the cuboid frame structures are covered by the filtering media, the body fluid can not only pass the filtering media arranged on the four side walls A1-A4 but also the filtering media arranged on the bottom area A5 of the frame structure of the filter system. Thus, the surface area available for filtering the body fluid is increased. The surface increase may be up to 8-15% compared to a filter system without a filtering media arranged on the bottom part of the frame structure.

The filtering bottom halves the time to get the first drop of blood filtered through the filter system. This is especially relevant for low volumes specifically in paediatrics. The recovery is maximized, especially for low volumes and at the same time collection time is minimized, especially relevant in case of emergency wash, such as massive bleeding for paediatrics.

In an embodiment of the present filter assembly the filtering media consists of at least to two materials, wherein the first material is a defoaming material made of a monofilament woven open mesh fabric and the second material is a depth filter material made of a spunbond nonwoven fabric or a polyurethane foam. It is to be understood that the materials can be arranged in layers, for example the defoaming material may be a first layer and the depth filter material may be a second layer, wherein the first and second layer are in contact to each other.

Defoaminq Material

The defoaming material or layer has preferably an embossed three dimensional structure configured, in particular for entrapping foam built up in the body fluid. The use of a defoaming material or layer with an embossed 3D structure removes or reduces foam. The underlying mechanism may be an entrapment of the foam within the defoaming layer. The spatial 3D structure allows for an entrapment of gas bubbles formed in the body fluid; i.e. gas bubbles are entrapped within the spatial structure.

The embossed 3D structure may be in form of a diamond pattern with regularly arranged protrusions and depressions of a certain height. One can describe the spatial pattern also as a zig-zag-structure or pyramided like structure.

As mentioned previously, the defoaming layer is a structured open mesh fabric.

In an embodiment the defoaming layer comprises a mesh opening between 100-500 µm, in particular between 150-400 µm, in particular between 200-350 µm, and more particular between 250-300 µm, for example 250 µm.

The mesh count of the open mesh fabric forming the defoaming layer is between 10-50 n/cm, in particular between 10-30 n/cm, more particular between 10-20 n/cm, such as 12-16 n/cm.

The fabric of the defoaming layer is made of monofilament fibers with a diameter between 100-350 µm, in particular 150-300 µm, more particular 200-300 µm, such as 200, 250, 300 µm. The monofilament fibers can be made of any thermoplastic material, but preferably of polypropylene (PP), polyethylene (PE), polyether ether ketone (PEEK) and others. Polypropylene is the most preferred one.

The defoaming layer can have a weight of 50-250 $g/m^2$, in particular 100-200 $g/cm^2$, more particular 150-200 $g/cm^2$, such as 98-103 $g/cm^2$, 180-190 $g/cm^2$, 156 $g/cm^2$.

The thickness of the defoaming layer may be 150-650 µm, in particular 200-500 µm, in particular 250-400 µm, in particular 300-350 µm.

The defoaming layer may also be of a sponge-like structure, for example made of polyurethane or polyester foam.

Depth Filter/Pre-Filter

As mentioned, the depth filter material or prefilter material is made of a polyurethane foam, in particular of a polyester polyurethane reticulated foam, or a spunbond nonwoven fabric.

In case of a non-woven fabric, the fibers are arranged such that gaps are formed between the randomly deposited fibers. The gaps can be defined as openings with an average pore size. Consequently, a pore size of the non-woven fabric results.

The pore size of the pre- or depth filter material is smaller than the upstream defoaming layer but may be larger than a downstream mesh filter material, which is described further below.

In an embodiment, the prefilter material or layer comprises or essentially consists of a spunbond nonwoven fabric. The individual fibers of this fabric may have any desired cross-section, such as a circular, elliptic rectangular, quadratic or triangular cross-section. Mixtures of fibers having different cross sections are also possible.

The fibers of the prefilter layer can also generally have any shape. However, it turned out that particularly good filtering can be achieved if the fibers, or at least a part of the fibers, comprise at least one groove extending in the longitudinal direction of the respective fiber. To give an example, the fibers may comprise three grooves each extending in a longitudinal direction of the fiber. Then, aggregates, fat and/or platelets can be particularly well filter from blood or another body fluid flowing through the filter assembly.

In an embodiment, at least a part of the fibers has a lobate cross-section. Such a lobate cross-section can be achieved, in an embodiment, by forming a groove in the fibers in the longitudinal direction. A trilobal cross-section is a particularly well suited example of a lobate structure. Such trilobal fibers are generally known, e.g., from WO 2013/110694 A1, the entire content of which is hereby incorporated by reference.

The fibers making up the non-woven fabric of the prefilter layer can be, in an embodiment, spunbond fibers or melt-blown fibers. While spunbond fibers typically have a fiber diameter that is at least 20 µm or larger, melt-blown fibers may have lower diameters of less than 20 µm.

The prefilter layer comprises or essentially consists of continuous filament spunbond nonwoven fabric. Said fabrics are obtained in continuous filament nonwoven processes (meltblowing and spunbonding) that start extruding chips or pellets of raw material. The length of the filament is theoretically infinite.

The fibers of the prefilter material may be monocomponent, bicomponent or multicomponent fibers, including "island in the sea" fibers. The fibers may consist of one polymer or a blend of polymers. Suitable materials for the fibers are, for example, a polyester, polyethylene, polypropylene, polybutylene, polymethylpentene, polyethylene terephthalate, polytrimethylene terephthalate, polybutylene terephthalate, poly(butylene terephthalate-co-polyalkylene glycol terephthalate), nylon 6,6, nylon 6,9, nylon 6/12, nylon 11, nylon 12, cellulose acetate, cellulose acetate propionate, or a combination thereof. Thereby, a non-hydrophobic or hydrophilic material is particularly appropriate to produce the fibers. It is also possible to increase the hydrophilicity of the material which is used to produce the fibers or to increase the hydrophilicity of the already produced fibers. Thereby, a physical treatment is more appropriate than the deposition of chemicals because such chemicals might potentially be leached from the fibers or the fabric produced therefrom during use of the filter assembly.

In one embodiment of such a spunbound depth material, the pore size of the pre- or depth filter material or layer is in a range of between 20 and 150 µm, in particular between 30 and 140 µm, in particular between 40 and 130 µm, in particular between 50 and 120 µm, in particular between 60 and 110 µm, in particular between 70 and 100 µm, in particular between 80 and 90 µm. Ranges of 100 to 130 µm, 105 to 125 µm, 70 to 90 µm, 75 to 85 µm, 30 to 45 µm and 35 to 40 µm are particularly appropriate.

In another preferred embodiment a polyurethane foam, in particular a polyester-polyurethane foam, is used as depth filter. The size of the open cells in the polyurethane foam is between 100 and 300 mm, preferably between 150 and 250 µm, more preferably between 200 and 240 µm, in particular 240 µm or 80 pores per linear inch (ppi).

Mesh Filter/Sieve

In a further embodiment the filtering media of the present filter assembly may consist of at least three materials, wherein the first material is a defoaming material made of a monofilament woven open mesh fabric, the second material is a depth filter material made of a spunbond nonwoven fabric or a polyurethane foam and the third material is a mesh filter material. The three materials may be arranged in layers such as a first defoaming layer, a second depth filter layer and a third mesh filter layer. It is to be understood that every layer may consist of sub-layers, like two or three sub-layers.

In an embodiment, the mesh layer material is made of a plurality of interconnecting threads forming a grid or a net. Thus, vertically arranged threads and horizontally arranged threads are connected to each other at connecting points so as to form a grid.

In an embodiment, the threads or filaments of the mesh filter layer have a circular cross-section. However, other cross sections, such as an elliptic, a rectangular, a quadratic or a triangular cross-section would also be possible. Likewise, mixtures of threads or filaments having different cross sections are also possible.

In an embodiment, the mesh size of the mesh filter layer is in a range between 20 and 160 µm, in particular between 30 and 140 µm, in particular between 40 and 130 µm, in particular between 50 and 120 µm, in particular between 60 and 110 µm, in particular between 70 and 100 µm, in particular between 80 and 90 µm. Ranges of 100 to 130 µm, 105 to 125 µm, 70 to 90 µm, 75 to 85 µm, 30 to 45 µm and 35 to 40 µm are particularly appropriate. The most preferred mesh sized are 40 µm and 120 µm.

In an embodiment, the mesh filter material can comprise or can be entirely made of a polymer such as a polyester, polyethylene, polypropylene, polybutylene, polymethylpentene, polyethylene terephthalate, polytrimethylene terephthalate, polybutylene terephthalate, poly(butylene terephthalate-co-polyalkylene glycol terephthalate), nylon 6,6, nylon 6,9, nylon 6/12, nylon 11, nylon 12, cellulose acetate, cellulose acetate propionate, or a combination thereof. Thereby, a non-hydrophobic or hydrophilic material is particularly appropriate to produce the mesh filter layer. It is also possible to increase the hydrophilicity of the material which is used to produce the mesh filter layer or to increase the hydrophilicity of the already produced filter. Thereby, a physical treatment is more appropriate than the deposition of chemicals because such chemicals might potentially be leached from the mesh filter during use of the container.

In an embodiment, the filter assembly does not comprise any anti-foaming agents. By avoiding the use of such anti-foaming agents the risk of leaching anti-foam chemicals into a fluid that is flowing through the filter assembly is fully prevented. This enhances the quality of the fluid filtered by the filter assembly.

Frame Structure

As described above, the filter system comprises a cuboid frame structure with six surface areas A1-A6; wherein the surface areas A1 and A2, A3 and A4, A5 and A6 are in each case opposite to each other.

At least five of the six surface areas A1-A5 are covered by a filtering media, and the remaining surface area A6 is in contact with the filter holder.

This sixth rectangular area A6 of the filter system, which is not covered by the filtering media, but is instead in contact with the filter holder, is covered by plastic material with a circular opening or recess as inlet for the body fluid into the interior of the filter system. Furthermore, this circular opening receives a projection of the filter holder for establishing the contact between filter holder and filter system. Filter holder and filter system are finally connected by gluing or welding at this contact area.

The fifth rectangular area A5 (or the bottom) of the filter system, which is opposite to the surface area A6, and the surface area A6 are connected to each other by at least two struts. Furthermore, the rectangular frame of are A5 contains at least one cross brace.

The frame structure of the filter system is preferably made of plastic, in particular acrylnitril-butadien-styrol (ABS) or poylcarbonate or polypropylene, by injection moulding.

Filter Holder

The filter holder is preferably a plastic element. It comprises means for contacting the filter system, in particular a cylindrical projection for contacting the circular opening of the sixth surface area A6 of the filter system. Said projection intrudes/projects into opening of the surface area A6 of the filter system and further establishes a connection to the interior of the filter system.

In a preferred embodiment the filter holder is injection molded with a stepped or graduated projection on one side; e.g. a large oval projection from which a smaller circular projection extends and wherein the smaller circular projection establishes the contact with the surface area A6 of the filter system.

In the assembled state of the final container system the filter holder is covered by a lid that comprises different inlets for blood and connectors for vacuum and safety values. This is described for example in WO 2020/254871 A1.

The present invention relates in an aspect to the use of the filter assembly having the features explained above for filtering a body fluid in vitro. Thereby, the body fluid can be blood, urine, bile, tissue fluid, sperm, lymph, saliva or cerebrospinal fluid. Blood is a particularly appropriate body fluid to be filtered.

In a further aspect, the present invention relates to a method of filtering a body fluid by letting the body fluid flow through a filter assembly according to the preceding explanations. The flow of the body fluid can be accomplished by gravity or by applying external forces such as low pressure to the body fluid or a container into which the filter body fluid is to be drawn. This method can be done in vitro or while a patient donating the body fluid to be filtered is connected to a filter appliance in which the body fluid is filtered.

In an embodiment, the method is a medical method for drawing intraoperative cell salvage (ICS) from a patient in need thereof. ICS is typically used for patients undergoing surgery or invasive procedures and is intended to provide those patients with an autotransfusion of blood or blood components. More details on such a method are given in subsequent sections.

In yet a further aspect the present invention relates to a container for collecting a body fluid comprising a filter assembly as described in detail above.

Such a container comprises a container housing with a body fluid inlet that allows a body fluid to enter an inlet section of the container housing. The container housing furthermore comprises a body fluid collection section and a vacuum connector for connecting a vacuum source to the container housing. In doing so, a negative pressure can be applied to the inlet section and to the body fluid collection section. Thereby, the vacuum source is typically connected via a vacuum line to the vacuum connector of the container housing.

Furthermore, the container housing comprises the filter assembly that separates the inlet section from the body fluid collection section. To be more specific, the filter assembly is arranged between the inlet section and the body fluid collection section so that a body fluid needs to pass the filter in order to flow from the inlet section to the body fluid collection section.

In particular, the filter assembly is arranged between the inlet section and the body fluid collection section, such that the defoaming layer faces the inlet section and the mesh filter layer faces the body fluid collection section.

In an embodiment, the container housing comprises a hydrophobic filter (i.e. separate from the filter assembly) that is arranged between the body fluid collection section and the vacuum connector. Thereby, the term "between" relates to a flow direction of air drawn by a vacuum source from the container (or the body fluid collection section of the container housing) during the intended operation of the container. I.e., any fluid that is drawn from the interior of the container housing (in particular air and smoke) needs to pass the hydrophobic filter prior to entering a vacuum line connected to the vacuum connector. Thus, the hydrophobic filter serves as protective element for a vacuum line being connected to the vacuum connector of the container housing, when vacuum is generated by a vacuum pump.

The filter system and the hydrophobic filter synergistically act together so that this combination results in the effects explained in the following. By constructing the filter assembly with a filter holder and a filter system comprising a defoaming layer, a prefilter layer and a mesh filter layer, much more flexibility is given for the design of the filter holder than in case of using prefabricated filter sockets like in prior art.

Furthermore, it is possible to manufacture the filter holder together with the filter system in a single manufacturing step, and the connection of the co-molded filter assembly component to the container is easily automatable. This significantly reduces manufacturing costs and increases the performance of the container due to more reliable and reproducible manufacturing steps.

The additional hydrophobic filter arranged in flow direction before the vacuum connector serves both as overfill protection and as smoke filter. Thus, it combines the properties of these elements, which are used in form of individual components according to prior art, in a single element. This single element is thereby included in the container housing. Thus, it is not necessary to connect it with a separate vacuum line. There is no need to clean and/or sterilize the hydrophobic filter. Rather, it can be designed as disposable that is discarded together with the whole container. This additionally facilitates the use of the container.

Using a filter system comprising a defoaming layer, an optional prefilter layer and a mesh filter layer instead of a regular filter (made only of fibers or foam or a membrane) is connected to the effect that extremely reproducible filtering conditions can be met. While regular filters have an average pore size with many pores being bigger or smaller than the average pore size, a mesh filter has a clearly defined mesh size that essentially does not vary. Besides, the use of the defoaming layer reduces or even prevents foam formation.

In an embodiment, a top cover or an inlet section of the container housing and the filter holder are manufactured as one piece, i.e., they are integrally formed. This facilitates the manufacturing steps significantly since no manual attachment of a filter to the container housing is necessary anymore. To give an example, the filter holder and (at least parts of) the container housing can be co-molded in one single injection molding step. Then, an outlet of the inlet section of the container housing turns integrally into an inlet of an interior of the filter holder. Any body fluid that enters the inlet section will then flow or will be drawn from the inlet section of the container housing towards an interior space of the filter holder. It has then to pass the filter system in order to reach the body fluid collection section.

As mentioned previously, the filter holder and the filter system are free of antifoam agents. While certain antifoam agents are necessary in case of regular filters to avoid an undesired foaming of blood, the design of the blood path through the filter element tend to induce foam formation in blood only to a very low extent. If no antifoam agents are used, no such agents can be leached into body fluids so that no corresponding contamination of the body fluid needs to be feared.

In an embodiment, the hydrophobic filter is integrated into the top cover of the container housing. Then, it is arranged in an upper location of the container so that the risk of getting into contact with the body fluid is significantly reduced. Furthermore, such integration in the top cover of the container still allows a compact design of the whole container.

The hydrophobic filter comprises, in an embodiment, a filter housing and a filter material placed in the filter housing. While it would be generally possible to design the hydrophobic filter as exchangeable element, it is intended, in an embodiment, that the hydrophobic filter is a disposable element that is discarded together with the whole body fluid collecting container. The lifetime of the hydrophobic filter is generally longer than the lifetime of the body fluid collecting container so that it is generally not necessary to replace the hydrophobic filter during the intended operation of the body fluid collecting container.

The hydrophobic filter may also be a mesh filter, wherein a mesh size of 2 to 20 μm, in particular 3 to 19 μm, in particular 4 to 18 μm, in particular 5 to 17 μm, in particular 6 to 16 μm, in particular 7 to 15 μm, in particular 8 to 14 μm, in particular 9 to 13 μm, in particular 10 to 12 μm is appropriate.

The hydrophobic filter is intended to filter air drawn by a vacuum source from the container for collecting a body fluid, or, to be more precisely, from the body fluid collecting section of this container. The hydrophobic filter protects the vacuum source from smoke (in particular surgical smoke), particles (such as bone or tissue fragments), and blood and also reduces the load of contaminations of the hydrophobic antibacterial filter that is associated to the pump and thus located downstream from the hydrophobic filter.

In an embodiment, the hydrophobic filter comprises a filter material comprising or consisting of a hydrophobic polymer such as polytetrafluoroethylene (PTFE), in particular expanded PTFE (ePTFE).

In an embodiment, the hydrophobic filter comprises a filter material comprising or consisting of a non-hydrophobic polymer such as polyester (such as PET) treated with a hydrophobic polymer, in particular a hydrophobic PET mesh. Since the contact with blood of this element is occasional and very limited in time (spurts) and due to the position (top cover), the risk that the hydrophobic treatment is leached into the blood is minimal. However, the hydrophobic treatment has to be biocompatible.

In an embodiment, the hydrophobic filter comprises a pleated filter material. By pleating the filter material, the effective filter surface can be increased while not increasing the overall space needed for the hydrophobic filter.

In an embodiment, the pleated filter material has a filter surface area being at least 3 times, in particular at least 4 times, in particular at least 5 times, in particular at least 6 times, in particular at least 7 times, in particular at least 8 times as high as the surface area of the filter element that houses the hydrophobic filter. The filter surface area might be 3 to 8 times, in particular 4 to 7 times, in particular 5 to 6 as high as the surface area of the filter element that houses the hydrophobic filter. E.g., if the filter element has a surface area of 5 to 20 cm$^2$, the total filter surface might be in a range of 15 to 160 cm$^2$. Thus, by such an arrangement it is possible to incorporate a quite big filter surface area in a filter element that has only very low space requirements. This facilitates incorporating the hydrophobic filter into the top cover of the container housing while not increasing the dimensions of the top cover as compared to the top covers known from prior art.

In an embodiment, the container is specifically adapted to receive blood as body fluid. I.e., the body fluid referred to in the present description is, in this embodiment, blood.

In an aspect, the invention relates to a body fluid collecting arrangement comprising a vacuum source and a container according to the preceding explanations. Thereby, the vacuum source is directly connected to a vacuum connector of the container via a vacuum line. No component parts other than the vacuum line is present between the vacuum source and the container.

Body fluid collecting arrangements known from prior art have the following general setup: body fluid collecting container—vacuum line—overfill protection—smoke connector—smoke filter—vacuum line—vacuum pump. Thus, six connection points need to be established in total. If the vacuum source is directly connected to the connector like in the currently discussed aspect of the present invention, only two connection points need to be established: body fluid collecting container—vacuum line—vacuum source. Thus, the integration of the hydrophobic filter into the container housing of the body fluid collecting container renders a separate overflow protection, a separate smoke connector and a separate smoke filter superfluous. Three separate parts each having two connecting points can be fully skipped when relying on this aspect of the present invention. This significantly reduces the workload for medical staff preparing a body fluid collecting arrangement ready to be used.

In case of massive overflow of the body fluid collecting section of the container housing, it might happen that the collected body fluid passes through the hydrophobic filter. Then, the body fluid might enter the vacuum line that is connected to the vacuum connector of the container housing. In an embodiment, the vacuum line comprises a hydrophobic antibacterial filter to protect the pump. Then, such overflow of small amounts of body fluids will not have any consequences. Rather, some hydrophobic vacuum lines are able to keep working also in the presence of accumulation of contaminations or liquids. The guiding principle, is to reduce complexity of assembly of the vacuum line to enhance usability.

In an embodiment, the vacuum line comprises an integrally formed antibacterial filter. Thus, this antibacterial filter does not represent an additional component part, but rather is an integral part of the vacuum line.

In an embodiment, the antibacterial filter is a hydrophobic filter. Then, it can also be used to effectively prevent any liquid that has entered the vacuum line, e.g., due to overfill events of the body fluid collection section of the container housing, from entering into the pump being arranged downstream of the antibacterial filter. It is possible to equip such an antibacterial filter with an additional chamber to accommodate any contaminations of the filter. Then, such chamber can also serve for receiving excessive body fluid drawn through the vacuum line due to an overfill event.

In an embodiment, the antibacterial filter has a pore size or mesh size that is sufficiently small to also filter viruses out of the fluid (in particular air) drawn through the vacuum line. In such a case, the antibacterial filter has also anti-viral properties. Then, it can be denoted as anti-viral filter.

In an aspect, the present invention relates to a method for manufacturing a container according to the preceding explanations. Thereby, a top cover of a container housing of the container and a filter holder of the container are co-molded. I.e., they are manufactured as one piece or, expressed in other words, they are integrally formed or integrally molded. Such a manufacturing process is significantly easier than the manufacturing processes known from prior art. It combines the previous method steps of producing a container housing and subsequently attaching a filter into the container housing into one single manufacturing step, namely a co-molding step. It can be accomplished, e.g., by injection molding.

While it is also possible to co-mold the filter assembly together with the filter holder, other approaches are taken in an embodiment of the manufacturing method. To be more precisely, in this embodiment, the filter assembly is applied (e.g., by molding) into the filter holder after the filter holder has been produced. Thereby, the filter holder itself may be co-molded with the top cover of the container housing. In doing so, it is not necessary to produce different molds for different mesh sizes to be applied for a filter module of the container housing. Rather, in this embodiment, only a single mold is necessary to produce a large number of container housing top covers with an integrally formed filter holder, wherein afterwards different filter assemblies filters can be applied into the filter holder, thus resulting in container housing top covers providing different filter properties (in particular different mesh sizes of the filter assembly).

In an aspect, the present invention relates to medical method for drawing intraoperative cell salvage (ICS) from a patient in need thereof. ICS is typically used for patients undergoing surgery or invasive procedures and is intended to provide those patients with an autotransfusion of blood or blood components. This method comprises the steps explained in the following. First, a blood suction line is connected to a blood inlet of a container for collecting blood. Furthermore, vacuum line is connected to a vacuum connector of this container and to a vacuum source, such as a vacuum pump. In doing so, a low pressure can be applied to an interior of the container, when the vacuum source is activated. The container is a container according to the preceding explanations. Thus, it comprises a container housing with the blood inlet that allows blood to enter an inlet section of the container housing. The container housing furthermore comprises a blood collection section. Thereby, the vacuum source is typically connected via a vacuum line to the vacuum connector of the container housing.

If all elements are assembled, the vacuum source is activated. Then, blood is drawn from a patient (e.g., during a surgical intervention) through the blood suction line into the receiving section of the blood-collecting canister. It then passes the filter and reaches the blood-collecting section. Afterwards, it can be drawn from the blood-collecting container in order to be further processed and/or autotransfused to the patient.

In an aspect, the present invention relates to a method for manufacturing a filter assembly according to the preceding explanations. As already mentioned, such a filter assembly comprises a filter holder and a filter system comprising defoaming layer, a prefiltering or depth layer and a mesh filter layer.

All embodiments of the described filter assembly can be combined in any desired way and can be transferred to the described use, the described container for collecting a body fluid and the described methods, and vice versa in each case.

Further details of aspects of the present invention will be explained in the following with respect to exemplary embodiments and accompanying Figures. In the Figures.

Figure 1:
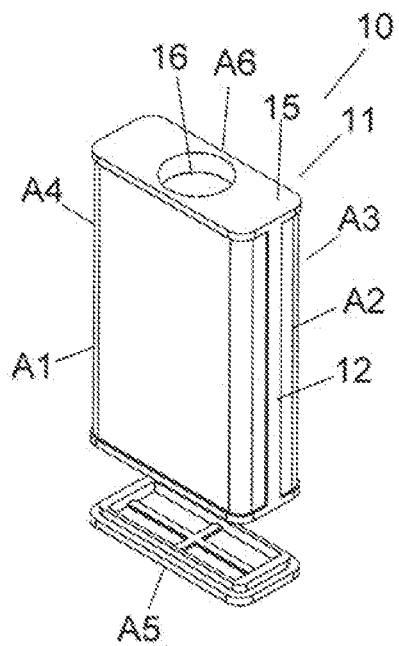
FIG. 1 is a perspective view of an embodiment of the filter system according to the invention.

FIG. 1 shows an embodiment of the filter system 10 having a cuboid frame structure 11 with six rectangular surface areas A1-A6. Five of the six surface areas A1-A5 are covered by a filtering media, and the sixth surface area A6 (here the upper side) is covered by plastic material with a circular opening as inlet 16 for the body fluid into the interior of the filter system.

The fifth rectangular area A5 (bottom side) of the filter system, which is opposite to the surface area A6, and the surface area A6 are connected to each other by at least two struts 12.

The fifth bottom area A5 is made of a plastic frame and with one or two cross braces. The plastic frame is injected moulded and welded to the frame structure.

Figure 2:
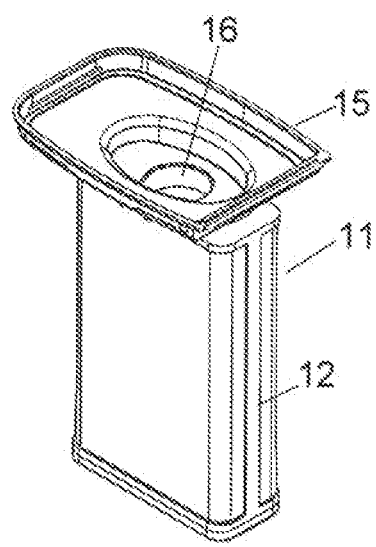
FIG. 2 is a perspective view of an embodiment of the filter assembly according to the invention comprising filter system and filter holder.

As shown in FIG. 2 the filter system 10 is connected to the filter holder 15. The filter holder 15 is a plastic element obtained by injection molding with a stepped/graduated projection on the lower side facing the filter system: an oval projection from which a small circular projection extends. Said circular projection is in turn in in contact with the surface area A6 of the filter system.

Figure 3:
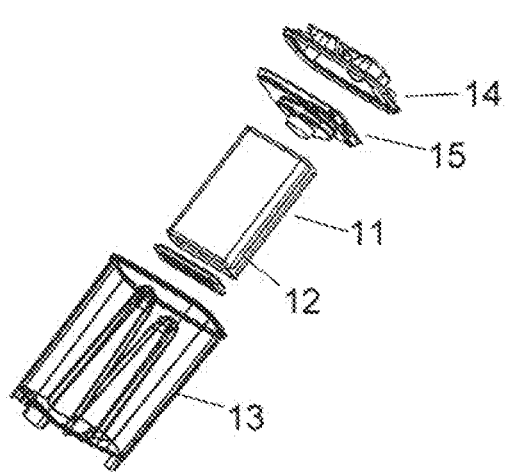
FIG. 3 is an explosive view of a blood collecting canister with a filter assembly according to the invention, a container for collecting the filtered body fluid and a lid
Figure 4:
FIG. 4 is a schematic view of the arrangement of FIG. 3 in the assembled state.

FIG. 3 shows an explosive view of a blood collecting canister with a filter assembly comprising the cuboid filter system and filter holder 15 according to the invention, a container 13 for collecting the filtered body fluid and a lid or top cover 14.

Blood enters the canister 13 housing through a blood inlet 16 in the top cover 14. The blood flows through the opening in the filter holder 15 into the interior of the filter system and passes the filter media. The filtered blood is collected in the blood-collecting section It can then be drawn through a blood outlet out of the blood-collecting canister in order to be further processed and/or auto-transfused to the patient.

What is claimed is:

1. A filter assembly for filtering a body fluid comprising a filter holder and a filter system downstream of the filter holder;
    wherein the filter system and the filter holder are in contact with each other,
    wherein the filter system comprises a cuboid frame structure with six rectangular surface areas A1-A6, and
    wherein five of the six surface areas A1-A5 are covered by a filtering media, and wherein the sixth surface area A6 is in contact with the filter holder; and
    wherein the filtering media comprises at least a first material and a second material and wherein the first material is a defoaming material made of a monofilament woven open mesh fabric and the second material is a depth filter material made of a spunbond nonwoven fabric or a polyurethane foam.

2. The filter assembly according to claim 1, wherein the defoaming material comprises a mesh opening between 100-500 µm.

3. The filter assembly according to claim 1, wherein the pore size of the depth filter material is in a range of between 20 and 150 µm.

4. The filter assembly according to claim 1, wherein the filtering media consists of at least three materials, wherein the first material is a defoaming material made of a monofilament woven open mesh fabric, the second material is a depth filter material made of a spunbond nonwoven fabric or a polyurethane foam and the third material is a mesh filter layer.

5. The filter assembly according to claim 4, wherein the mesh filter material has a mesh size in a range of between 20 and 150 µm.

6. The filter assembly according to claim 1, wherein the cuboid frame structure of the filter system is made of a thermoplastic material.

7. The filter assembly Filter according to claim 1, wherein the sixth rectangular area A6 of the filter system, which is in contact with the filter holder, is covered by plastic with a circular opening.

8. The filter assembly Filter according to claim 1, wherein the fifth rectangular area A5 of the filter system, which is opposite to the surface area A6, and the surface area A6 are connected to each other by at least two struts.

9. The filter assembly according to claim 7, wherein the filter holder comprises a cylindrical projection for contacting the circular opening of the sixth surface area A6 of the filter system.

10. The filter assembly according to claim 2, wherein the mesh opening is between 150-400 µm.

11. The filter assembly according to claim 3, wherein the pore size is between 30-140 µm.

12. The filter assembly according to claim 3, wherein the pore size is between 50-120 µm.

13. The filter assembly according to claim 4, wherein the mesh filter layer includes a mesh size between 30-140 µm.

14. The filter assembly according to claim 4, wherein the mesh filter layer includes a mesh size between 40-120 µm.

15. A method of filtering a body fluid in vitro using the filter assembly of claim 1 comprising:
    flowing the body fluid through the filter assembly.

16. The method of claim 15, wherein the body fluid is blood.

17. A container for collecting a body fluid, comprising a filter assembly according to claim 1.

18. The container according to claim 17, further comprising a container housing with a body fluid inlet though which body fluid can enter an inlet section of the container housing, a body fluid collection section, a vacuum connector for connecting a vacuum source to the container housing for applying a low pressure to the inlet section and the body fluid collection section, and the filter assembly as filter module being arranged between the inlet section and the body fluid collection section.

19. The container for collecting a body fluid according to claim 18, wherein the container housing additionally comprises a hydrophobic filter that is arranged between the body fluid collection section and the vacuum connector in flow direction of air drawn by a vacuum source from the body fluid collection section during intended use of the container.

* * * * *